United States Patent [19]
Hayashi et al.

[11] Patent Number: 5,317,925
[45] Date of Patent: Jun. 7, 1994

[54] DOUBLE-CANTILEVER BEAM TYPE TEST PIECE AND CORROSIVE ENVIRONMENTAL CRACK GROWTH MEASURING APPARATUS

[75] Inventors: Makoto Hayashi; Satoshi Kanno, both of Hitachi, Japan; Naoto Saito, Austin, Tex.

[73] Assignee: Hitachi, Ltd., Tokyo, Japan

[21] Appl. No.: 671,038

[22] Filed: Mar. 18, 1991

[30] Foreign Application Priority Data

Mar. 19, 1990 [JP] Japan ............................ 2-69073

[51] Int. Cl.$^5$ .................................... G01N 19/00
[52] U.S. Cl. .............................. 73/799; 422/53; 436/6
[58] Field of Search .............. 422/53; 436/6; 73/799

[56] References Cited

U.S. PATENT DOCUMENTS

| | | |
|---|---|---|
| 4,003,246 | 1/1977 | Cain ............................ 73/799 |
| 4,149,406 | 4/1979 | Russenberger ................. 73/799 |
| 4,198,870 | 4/1980 | Barker et al. ................. 73/799 |
| 4,677,855 | 7/1987 | Coffin, Jr. et al. ........... 73/799 |
| 4,711,131 | 12/1987 | Hopkins ....................... 73/799 |
| 4,763,528 | 8/1988 | Bouami et al. ................. 73/799 |

FOREIGN PATENT DOCUMENTS 62-177440 4/1987 Japan .

*Primary Examiner*—Timothy M. McMahon
*Attorney, Agent, or Firm*—Antonelli, Terry, Stout & Kraus

[57] ABSTRACT

A corrosive environmental crack length measuring apparatus including a double-cantilever beam type test piece having a tapered portion in a portion where the crack grows, a slit, and at least two holes, with the test piece being placed within a corrosive environment. Leads inserted in the holes of the test piece to be spot-welded thereto to supply a direct current to the holes. A current polarity switching device is provided with, a stabilized direct current power supply connected with the direct current supplying leads through the current polarity switching device. Potential difference measuring leads are inserted in holes formed in two outer faces of the double-cantilever beam type test piece parallel to a section of a crack growing portion at a plurality of points along the crack growing direction so as to be spot-welded thereto. A multiplexer is provided with, a micro-voltmeter connected with the potential difference measuring leads through the multiplexer, and an arithmetic unit judges crack length based on ratios between potential differences measured by switching the polarity of direct current using the current polarity switching device.

14 Claims, 14 Drawing Sheets

FLOW CHART OF WHOLE PROCESS OF CRACK GROWTH RATE MEASUREMENT AND CORROSIVE ENVIRONMENT MEASUREMENT

FIG. 19 FLOW CHART OF PROCESS OF CRACK LENGTH JUDGEMENT, CRACK GROWTH RATE MEASUREMENT AND CORROSIVE ENVIRONMENT MEASUREMENT

DOUBLE-CANTILEVER BEAM TYPE TEST PIECE AND CORROSIVE ENVIRONMENTAL CRACK GROWTH MEASURING APPARATUS

BACKGROUND OF THE INVENTION

The present invention relates to a double-cantilever beam type test piece and a corrosive environmental crack growth measuring apparatus, and more particularly, to a technique of measuring growth speed of a crack such as corrosion cracking, that is, a double-cantilever beam test piece (DCB sensor) which is capable of exhibiting nearly constant stress intensity factor at crack tip when applied with a load caused due to application of a fixed displacement irrespective of crack length, and a corrosive environmental crack depth measuring apparatus which is suitable for judging the degree of corrosive environment based on the crack growth rate calculated automatically from the change of crack depth with time obtained from measurements of the crack length in the test piece placed in the actual environment by on-line measurement using a direct current potential method.

Recently, it has become clear that since structures in a boiling water type reactor (BWR) are exposed to an intensive radioactive environment, stainless steel is caused to be sensitized by neutron irradiation to give rise to a problem that there is a good chance of generation of irradiation assisted stress corrosion cracking or what is called IASCC. As a method for controlling such IASCC, it has been proposed to inject hydrogen. In this method, injection of hydrogen contributes to reduction of concentration of dissolved oxygen and control of corrosive potential. According to this method, however, it becomes necessary to observe whether the IASCC is controlled or grows within the reactor. To cope with this, as an apparatus for measuring crack growth rate within a corrosive environment, General Electric Company, U.S. has proposed an apparatus for measuring crack length by applying a fixed displacement to (DCB sensor) utilizing a potential drop method (Japanese Patent Unexamined Publication No. 62-177440). This measuring apparatus is presently applied experimentally to actual reactors.

However, although it has been determined that distribution of stress intensity factor in DCB sensor is uniform and although the test piece is seven inches in overall length, the DCB sensor of the above conventional measuring apparatus has such characteristics that, as the crack grows by one inch, the stress intensity factor is reduced to 60% of the initial stress intensity factor, and the conventional DCB sensor is not suitable for measuring the crack growth rate with a proper stress intensity factor.

SUMMARY OF THE INVENTION

An object of the present invention is to provide a double-cantilever beam test piece and a corrosive environmental crack growth measuring apparatus which are capable of optimizing the configuration of DCB sensor so as to reduce the size of the same as well as make the stress intensity factor distribution nearly uniform, optimizing a method for measuring crack length by on-line measurement utilizing a direct current potential drop method, and automatically calculating crack growth rate by measuring crack length with high accuracy.

To achieve this end, according to the present invention, a double-cantilever beam type test piece is used for obtaining crack growth rate within a corrosive environment by being applied with a load due to application of a fixed displacement, wherein the configuration of a section of a portion where a crack grows is a tapered the width of which is reduced as crack depth increases.

Further, according to the present invention, a corrosive environmental crack length measuring apparatus comprises a double-cantilever beam type test piece which has a slit and at least two holes formed respectively in surfaces defining the slit on a fixed displacement application side thereof and which is placed in a corrosive environment, leads inserted in the holes to be spot-welded thereto for serving to supply a direct current to the holes, a current polarity switching device, a stabilized direct current power supply connected with the direct current supplying leads through the current polarity switching device, potential difference measuring leads inserted in holes formed in two outer faces of the double-cantilever beam type test piece parallel to a section of a crack growing portion at a plurality of points along the crack growing direction so as to be spot-welded thereto, a multiplexer, a micropotentiometer or voltmeter connected with the potential difference measuring leads through the multiplexer, and arithmetic and processing means for judging crack length based on ratios between potential differences measured by switching the polarity of direct current using the current polarity switching device.

In a double-cantilever beam type test piece according to the present invention, the section of a crack growing portion has tapered edges of a shape of a straight line or a curve of second power equation in the crack growing direction, and outer faces of the test piece perpendicular to outer faces thereof which are parallel to the section of the crack growing portion are tapered from a point corresponding to the crack growth starting point; therefore, it is possible to maintain the stress intensity factor nearly constant even if the crack grows.

In a corrosive environment crack length measuring apparatus according to the present invention, with the double-cantilever beam type test piece being placed within a corrosive environment, potential differences are detected between a plurality of selected points of the double-cantilever beam type test piece, measurements are performed by the measuring apparatus under the control of arithmetic and processing means such as a computer which performs the data processing as well, and the arithmetic and processing means is programmed to evaluate the crack length and crack growth rate; and therefore, it is possible to calculate the relationship between the crack growth rate and the corrosive environment automatically and accurately.

DESCRIPTION OF THE PREFERRED EMBODIMENTS

Figure 1:
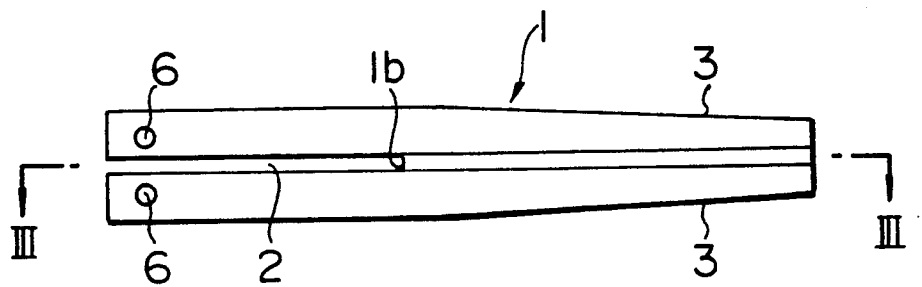
FIG. 1 is a front view of a DCB sensor according to a first embodiment of the present invention.
Figure 2:
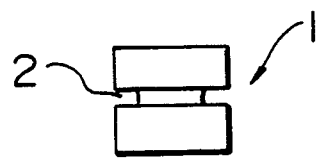
FIG. 2 is a left side view of the DCB sensor shown in FIG. 1.
Figure 3:
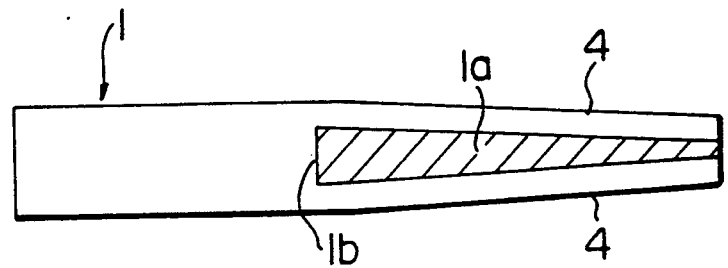
FIG. 3 is a sectional view taken along the line III—III of FIG. 1, showing a section of a crack growing portion of the DCB sensor.

FIGS. 1 to 3 show a double-cantilever beam type test piece or DCB sensor 1 according to an embodiment of the present invention.

As shown in FIG. 1, the DCB sensor 1 is formed in the center hereof with a slit 2 extending from its left-hand end surface toward a right-hand end surface. As shown in FIG. 3, a section 1a of a crack growing portion has a tapered shape that is wide at an initial crack portion 1b and narrows or tapers toward the right-hand side of the DCB sensor 1. As shown in FIGS. 1 and 3, the external form of the DCB sensor 1 includes tapered surfaces 3, 4 gradually reducing the sectional area thereof in a direction of crack growth. The tapered surfaces 3 are provided on a pair of outer faces which are parallel to the section where the crack grows, and the tapered surfaces 4 are provided on another pair of outer faces which are perpendicular to that section.

Figure 13:
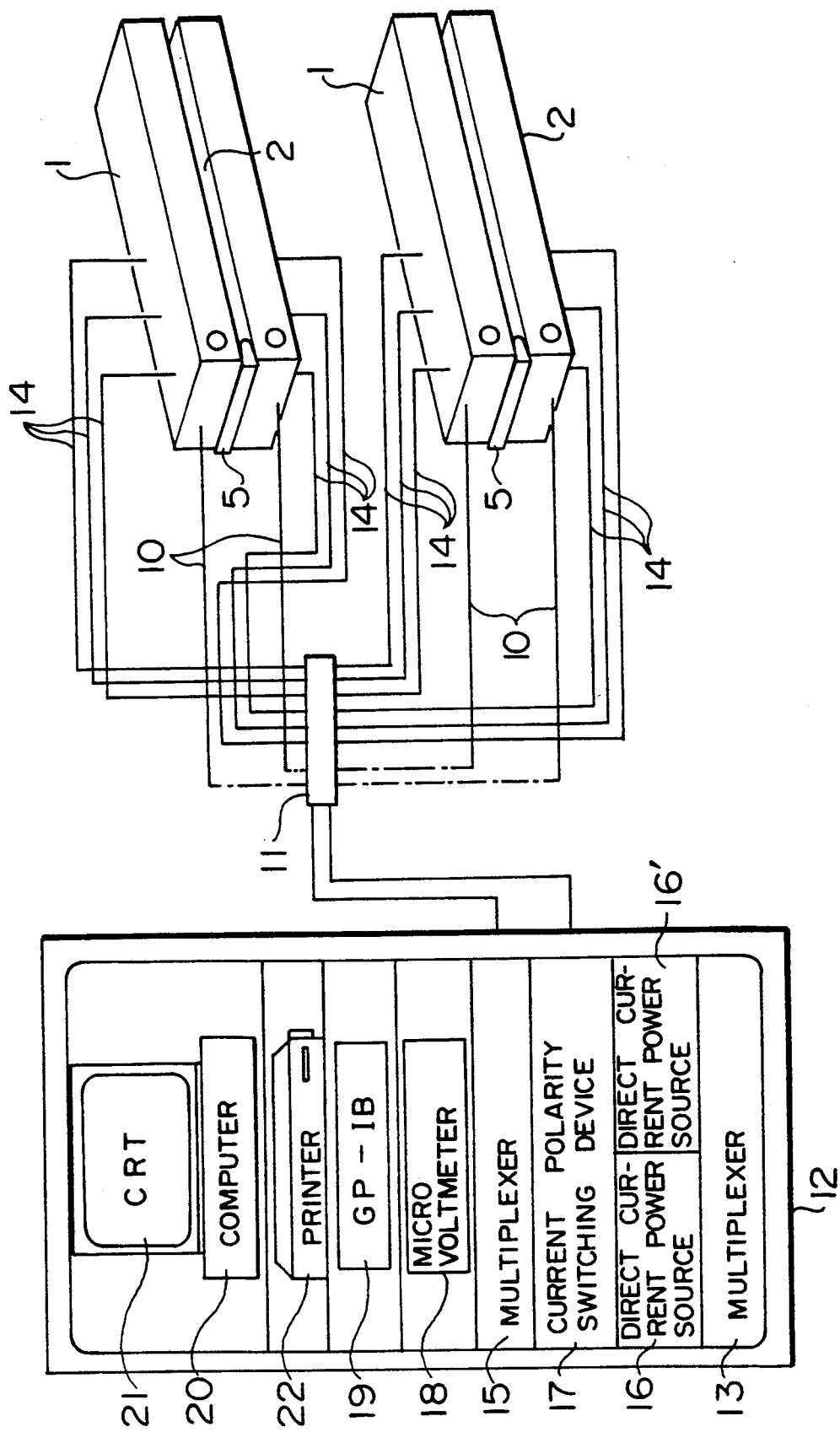
FIG. 13 is a schematic partially perspective view for explanation of a system for measuring crack length in the DCB sensor and monitoring water chemistry.

The DCB sensor 1 having the above-described configuration is set in a corrosive environment such as, for example, in high temperature water, so as to make the crack grow attributable to stress corrosion cracking in the following manner. Although not shown in FIG. 1, a wedge 5 of non-conductor is inserted in a slit 2 at the left end portion thereof as shown in FIG. 13 so as to apply a fixed displacement to the DCB sensor 1 to apply a load thereto, thus setting the stress intensity factor at crack tip at a value not less than a certain fixed value. More specifically, a fatigue crack performed in the DCB sensor 1 mechanically by a fatigue testing machine making use of two holes 6 formed on the left end side of the slit 2 is caused to grow to a predetermined length due to stress corrosion cracking within the corrosive environment, and thereafter, the wedge 5 is inserted into the slit 2 to cause the crack to grow further.

Figure 4:
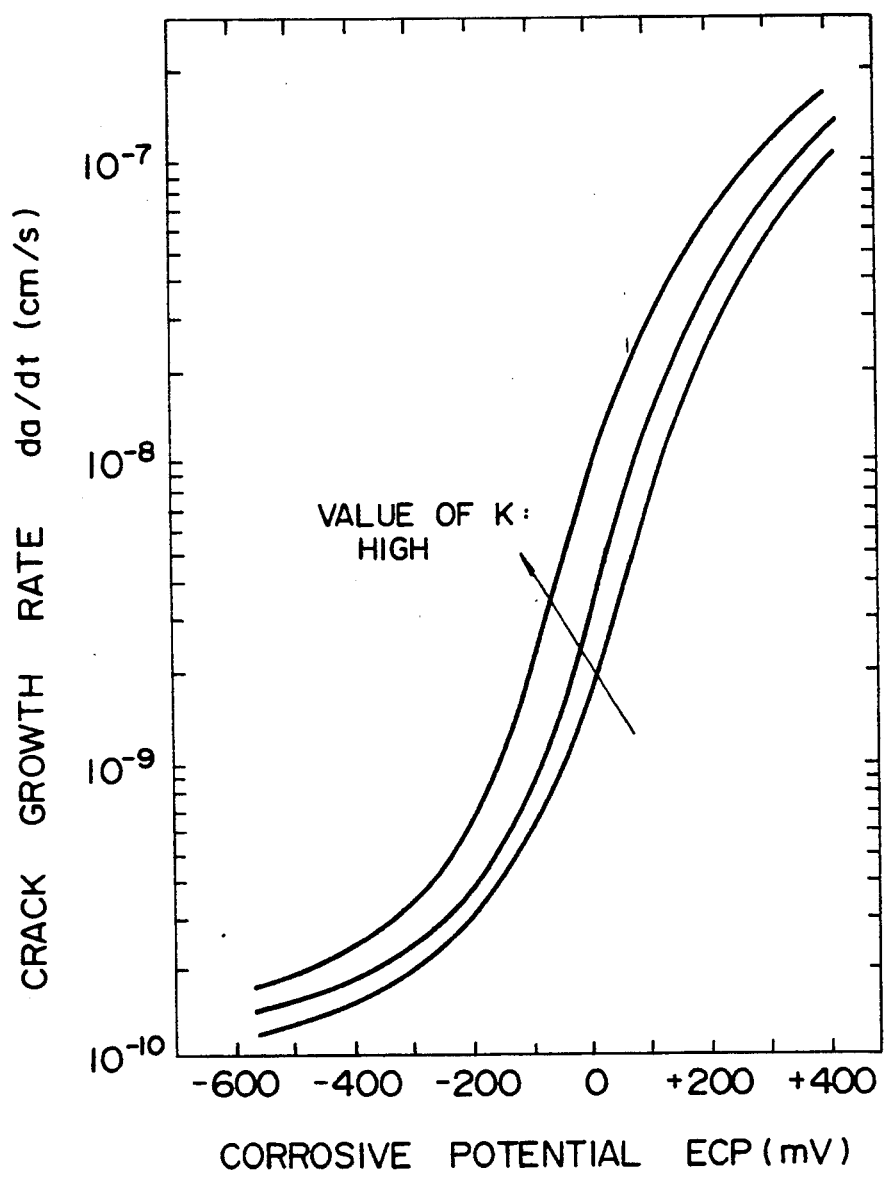
FIG. 4 is a graphical illustration of the relationship between the crack growth speed and the corrosive potential.

The crack has a characteristic that the growth rate thereof depends on the stress intensity factor and the degree of corrosive environment. In other words, with the same stress intensity factor, if one of the corrosive environmental conditions such as the concentration of dissolved oxygen, for example, is high the crack growth rate is high as well, while, if the concentration of dissolved oxygen is low, the growth rate is low as well. Further, as shown in FIG. 4, when the water chemistry is bad, that is, when the corrosive potential is high the crack growth rate becomes high, while when the corrosive potential is low the growth rate becomes low. On the other hand, the greater the stress intensity factor, the higher the crack growth rate becomes. Accordingly, by placing the DCB sensor 1 within the corrosive environment, the stress intensity factor of which is set at a proper value utilizing the wedge 5 so as to obtain the crack growth rate due to measurement of the crack length therein, it is possible to determine the degree of corrosive environment from the growth rate thus obtained. Namely, although not directly, the DCB sensor 1 can serve as a corrosion sensor. However, in the conventional DCB sensor, since the stress intensity factor decreases as the crack grows as noted above, a disadvantage resides in the fact that the corrosive environment should be evaluated from both the crack growth rate and stress intensity factor.

In the DCB sensor 1 of the structure shown in FIG. 1 according to the present invention, if the slit 2 has a sufficient length, the stress intensity factor at the crack tip does not vary so much even if the crack grows However, when the slit 2 does not have a sufficient length, the stress intensity factor decreases rapidly with an increase in the crack length. Decrease of the stress intensity factor caused with the increase of the crack length prevents the crack from further growing so that the function as a corrosion sensor is lost. On the other hand, if the initial stress intensity factor is set at a large value by increasing the thickness of the wedge 5 for the purpose of enabling the crack to grow even if the crack length is increased, the crack grows rapidly to reduce the service life of the corrosion sensor. In addition, in order to enable a setting within a measuring pipe such as LPRM disposed in the BWR, it is necessary to reduce the size of the corrosion sensor. With the above-described DCB sensor 1 according to the present invention, since, at least outer faces thereof which are parallel to the section where the crack grows are formed in a tapered shape, it becomes possible to make the stress intensity factor nearly constant even though the size is small for the following reasons.

Figure 5:
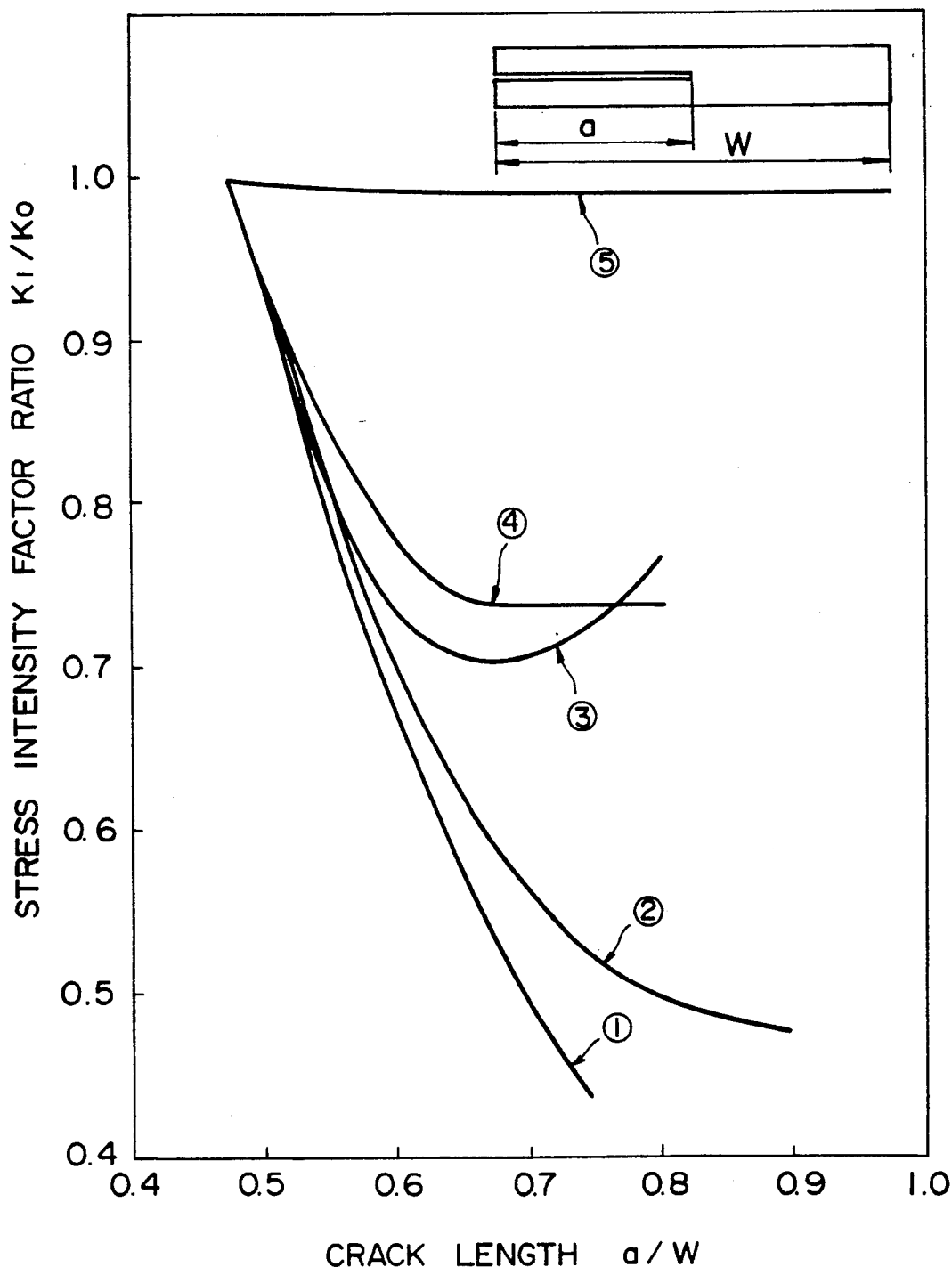
FIG. 5 is a graphical illustration of the change in the stress intensity factor ratio relative to the crack length in the DCB sensor.
Figure 6:
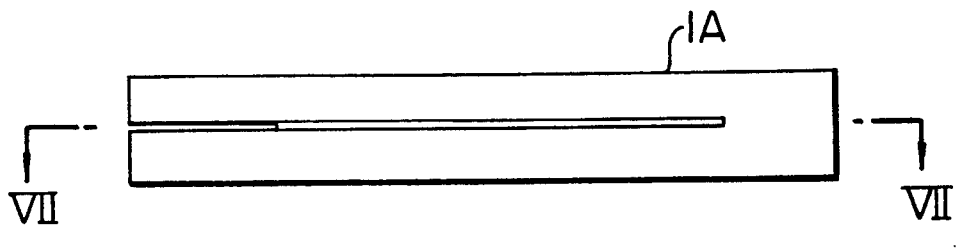
FIG. 6 is a front view of another DCB sensor.

FIG. 5 shows changes of the stress intensity factor relative to the crack length in DCB sensors of various configurations shown in FIGS. 6 to 12, the stress intensity factor being calculated from the crack tip stress distribution obtained by means of a finite-element method. The stress intensity factor $K_1$ and $K_0$, $K_0$ representing the stress intensity factor at the time when the crack length expressed as the ratio a/W is equal to 0.474. It is noted here that a represents the distance from the left end of the DCB sensor to the crack tip and W represents the overall length of the DCB sensor as shown in FIG. 5. A curve ① shows a distribution of the stress intensity factor ratio $K_1/K_0$ of a conventional DCB sensor 1A shown in FIGS. 6 and 7 in which no tapered portion is formed externally and the section of the crack growing portion is of the shape of a straight line. The stress intensity factor ratio $K_1/K_0$ shown by the curve ⓪ decreases rapidly with the crack length and $K_1/K_0$ becomes less than 0.5 when a/W=0.7. A curve ② shows a distribution of the stress intensity factor ratio $K_1/K_0$ of a DCB sensor 1A' shown in FIG. 8 in which the section of the crack growing portion is of a tapered shape. The stress intensity factor ratio $K_1/K_0$ shown by the curve ② decreases rapidly with the crack length and $K_1/K_0$ is about 0.5 when a/W=0.8, which means that the decreasing rate is smaller than that of the curve ①. Namely, it is understood that since the section of the crack growing portion is formed in the tapered shape the stress intensity factor can be made larger than that of the curve ① as the crack length increases. A curve ③ shows a distribution of the stress intensity factor ratio $K_1/K_0$ of a DCB sensor 1B shown in FIG. 9 and 10 which has an external form shown in these drawings and in which the tapering degree of the shape of the section of the crack growing portion is larger as compared with the case of FIG. 8. As shown in FIG. 5, in the region of a/W=0.65 to 0.7, $K_1/K_0$ is approximately 0.7 which is considerably improved as compared with that of the curves ① and ②. However, as the crack length increases further, the stress intensity factor ratio $K_1/K_0$ increases rather than decreases. In order to increase the stress intensity factor at portions of greater crack length, there is provided a DCB sensor 1B' shown in FIG. 11 the configuration of which is similar to that of the DCB sensor 1B shown in FIGS. 9 and 10 and in which outer faces parallel to the section of the crack growing portion are tapered. A curve ④ shows a distribution of the stress intensity factor ratio $K_1/K_0$ of the DCB sensor 1B'. As seen from the curve ④, in the region of a/W=0.63 to 0.85, $K_1/K_0$ is approximately 0.75 and maintained at nearly constant value. Accordingly, in case of using the DCB sensor 1B', if an examination is performed in the condition that a fatigue crack preformed in the sensor 1B' mechanically by a fatigue testing machine is made to grow to an extent of a/W=0.63 due to stress corrosion cracking within the corrosive environment and then a wedge is inserted into the slit, it is possible to permit the crack to grow while maintained the stress intensity factor nearly constant until an increment of a/W becomes 0.22 ($\approx$20 mm).

Figure 7:
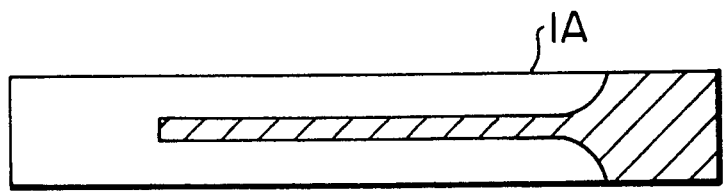
FIG. 7 is a sectional view of the DCB sensor taken along the line VII—VII of FIG. 6.
Figure 8:
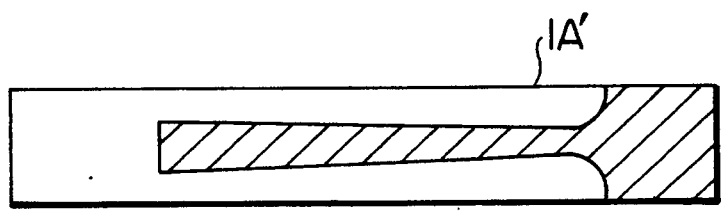
FIG. 8 is a sectional view of another DCB sensor similar to FIG. 7.
Figure 9:
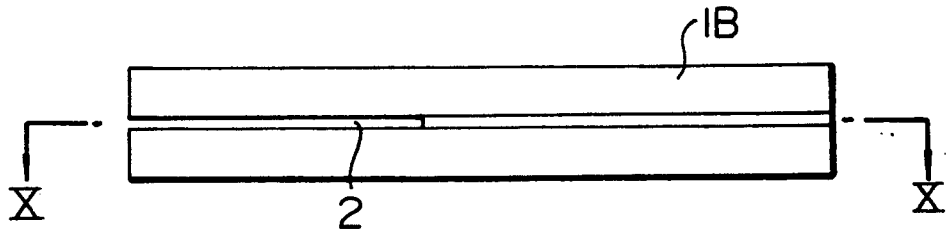
FIG. 9 is a front view of another DCB sensor.
Figure 10:
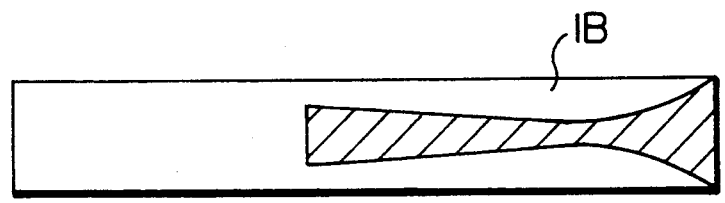
FIG. 10 is a sectional view of the DCB sensor taken along the line X—X of FIG. 9.
Figure 11:
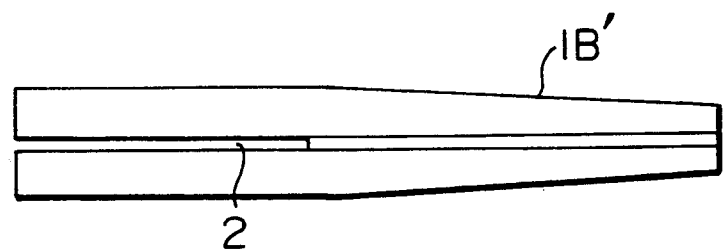
FIG. 11 is a front view of a further DCB sensor.
Figure 12:
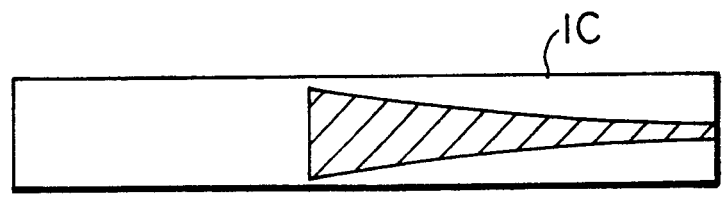
FIG. 12 is an illustration showing, in section, a crack growing portion of a different DCB sensor.

The DCB sensors shown in FIGS. 7, 8 and 10 have large widths in the section of their respective crack growing portions for the purpose of decreasing the stress intensity factor when the crack grows excessively long so as to prevent the crack from growing further. This is because there is a possibility that the crack in the section portion grows thoroughly to divide the DCB sensor into two parts to form loose parts under certain conditions of use of these DCB sensors. In case that such matter is out of question or in case that a protective tube is provided around the exterior of the DCB sensor so as to prevent the formation of loose parts even when the DCB sensor is divided into two parts, there is no need to minimize the stress intensity factor at portions of greater crack length. FIG. 12 shows a DCB sensor 1C in which the section of the crack growing portion has an edge shape that is formed not by a straight line but by a curve of a second power equation, and the width of the section is not enlarged but maintained as being narrow even at portions of greater crack length, thereby enabling the stress intensity factor to be maintained constant. The DCB sensor 1C is provided with tapers of a straight line on its external form line the DCB sensor 1B' shown in FIG. 11. A curve ⑤ of FIG. 5 shows a distribution of the stress intensity factor ratio $K_1/K_0$ of the DCB sensor 1C. It is seen from this distribution that $K_1/K_0$ is approximately 1.0 and maintained at nearly constant value in the region of a/W=0.5 to 0.95. Accordingly, if an examination is performed in the condition that a fatigue crack preformed in the DCB sensor 1C mechanically by a fatigue testing machine is made to grow slightly due to stress corrosion cracking within the corrosive environment and then a wedge is inserted into the slit, it is possible to permit the crack to grow while keeping the stress intensity factor nearly constant until an increment of a/W becomes about 0.45 (=42 mm).

In the aforementioned DCB sensor 1 shown in FIGS. 1 to 3, considering the characteristics of variation of the stress intensity factor of the DCB sensors having the above various forms shown in FIG. 5, the outer faces of the DCB sensor which are parallel to the section of the crack growing portion are tapered, the opposite edges of the section concerned are tapered and the outer faces of the DCB sensor which are perpendicular to the section concerned are tapered additionally.

As shown in FIG. 13, two leads 10 are attached to each of at least two DCB sensors 1 placed within a corrosive environment by spot welding for supplying a direct current to the DCB sensor 1. The leads 10 are connected with a current multiplexer 13 of a corrosive environment supervisory apparatus through a terminal box 11. The corrosive environment supervisory apparatus 12 serves to measure the crack length and monitor the water chemistry. Leads 14 for measuring potential differences are connected with a potential difference measuring multiplexer 15 through the terminal box 11. The direct current, supplied from two DC power sources 16, 16', is supplied to the DCB sensors 1 through the direct current supply leads 10 with its polarity reversed intermittently by a current polarity switching device 17. The potential difference measuring leads 14, having their measuring points switched by the multiplexer 15, are further connected with a microvoltmeter 18 where the potential differences are measured. The measured potential differences are transmitted to a computer 20 through a GP-IB interface 19. The current polarity switching device 17 and the multiplexers 13, 15 are controlled by the computer 20 through the GP-IB interface 19.

As the measurement is started, the computer 20 operates to calculate and record the crack length in the DCB sensor 1 from the data on the test time or operating time as well as from the potential differences measured at regular time intervals by making use of a method to be described hereinbelow. In this manner, a crack growth curve is obtained so that a crack growth rate is calculated from the gradient of this curve. As a result, the relationship between the crack growth rate and the stress intensity factor can be obtained, which relationship is displayed on a screen of a CRT 21 or printed out by a printer 22.

Figure 14:
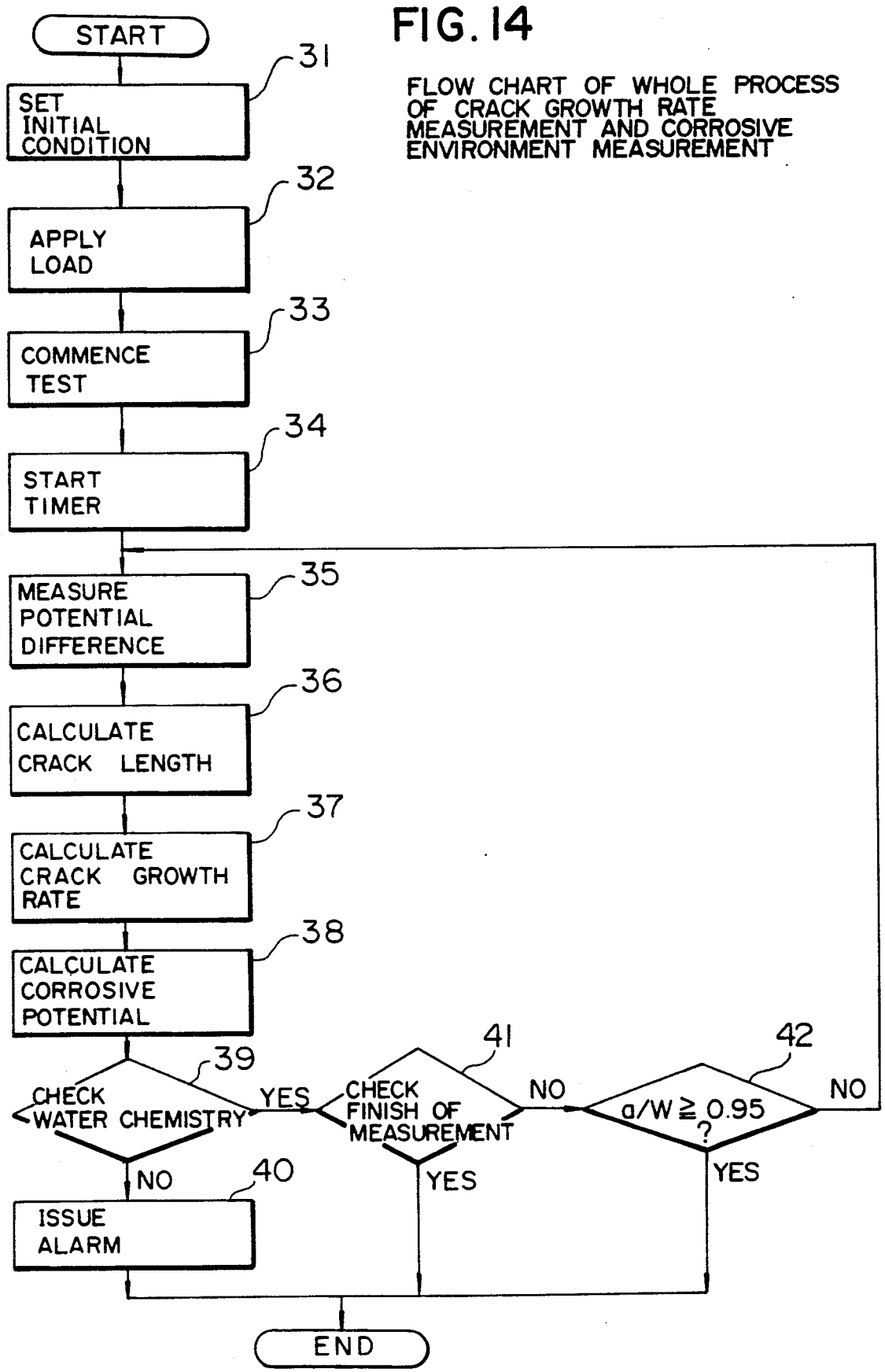
FIG. 14 is a flow chart of the whole process of measuring crack length and corrosive environment.

Next, description will be given of the measuring and monitoring functions of the corrosive environment supervisory apparatus 12 using the DCB sensors 1. FIG. 14 is a flow chart showing the whole process of measuring the crack growth rate and corrosive environment. At step 31, the DCB sensor 1 is attached and an initial condition of the corrosive environment including temperature and water chemistry is. At step 32, a fixed displacement is applied to the DCB sensor 1 by the wedge 5 so as to permit a load to be applied. At step 33, a test is commenced and, at step 34, a timer for measuring the test time is started. At step 35, the potential differences of the DCB sensor 1 are measured and, at step 36, the crack length a/W is calculated. Subsequently, at step 37, the crack growth rate is calculated and, at step 38, the corrosive potential is calculated. Based on the results thus obtained, the corrosive environment, particularly the water chemistry such as the concentration of dissolved oxygen, for example, is checked at step 39. If it is judged that the water chemistry is abnormal, the operation proceeds to step 40 at which an alarm is issued to interrupt the measurement or hydrogen is injected for restoring the water chemistry to normality. If it is judged that the water chemistry is normal at step 39, the operation proceeds to step 41 at which it is checked as to whether or not the measurement is finished. If it is judged that the measurement is being continued, the operation proceeds to step 42 at which it is checked whether or not the crack length a/W is not less than 0.95 or than 0.95, the operation returns to step 35 at which the potential differences are again measured to determine the the crack length. By repeating this process, the measurement is continued until the crack length a/W becomes 0.95.

Figure 15:
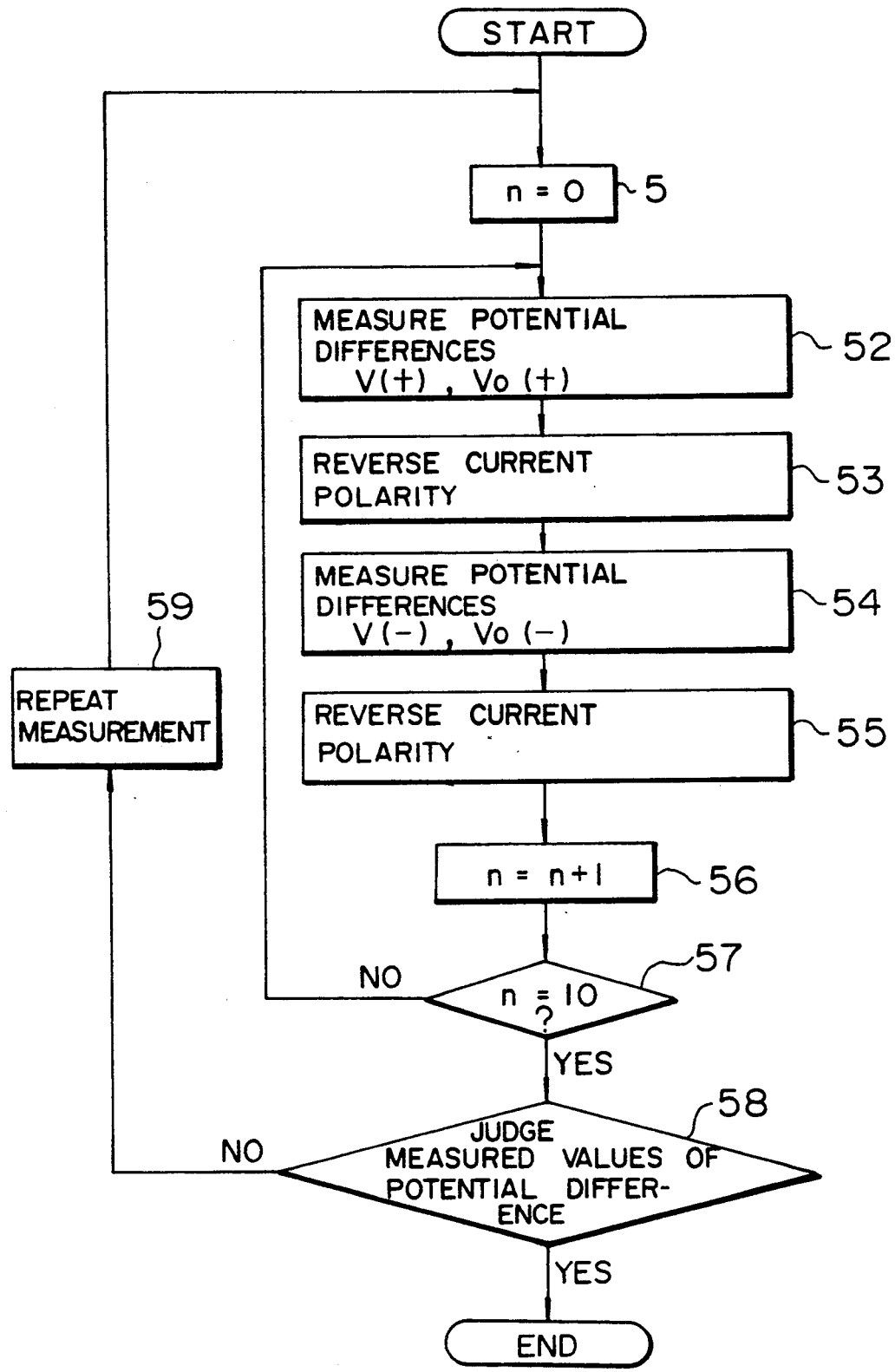
FIG. 15 is a flow chart of the process of potential difference measurement.

FIG. 15 is a flow chart showing the process of measuring the potential differences which are necessary for the measurement of the crack length in the DCB sensor 1. At step 51, the number of measurements n is reset as being 0 (zero). At step 52, potential differences $V_0(+)$ and $V(+)$ are measured when the current is positive, for example. At step 53, the polarity of the current is reversed by the current polarity switching device 17 and, at step 54, potential differences $V_0(-)$ and $V(-)$ are measured when the current is negative. At step 55, the polarity of the current is reversed so as to be returned to the initial polarity. At step 56, 1 (one) is added to n. At step 57, it is judged whether or not the number of measurements exceeds the fixed number 10, for example. If it is judged that the number of measurements does not reach 10, the operation returns to step 52. If it is judged that the number of measurements has reached 10, the operation proceeds to step 58 at which it is judged whether or not the measured values of potential difference are normal or not. If it is judged to be abnormal, the operation proceeds to step 59 at which the measurement is repeated again and then returns to step 51.

Figure 16:
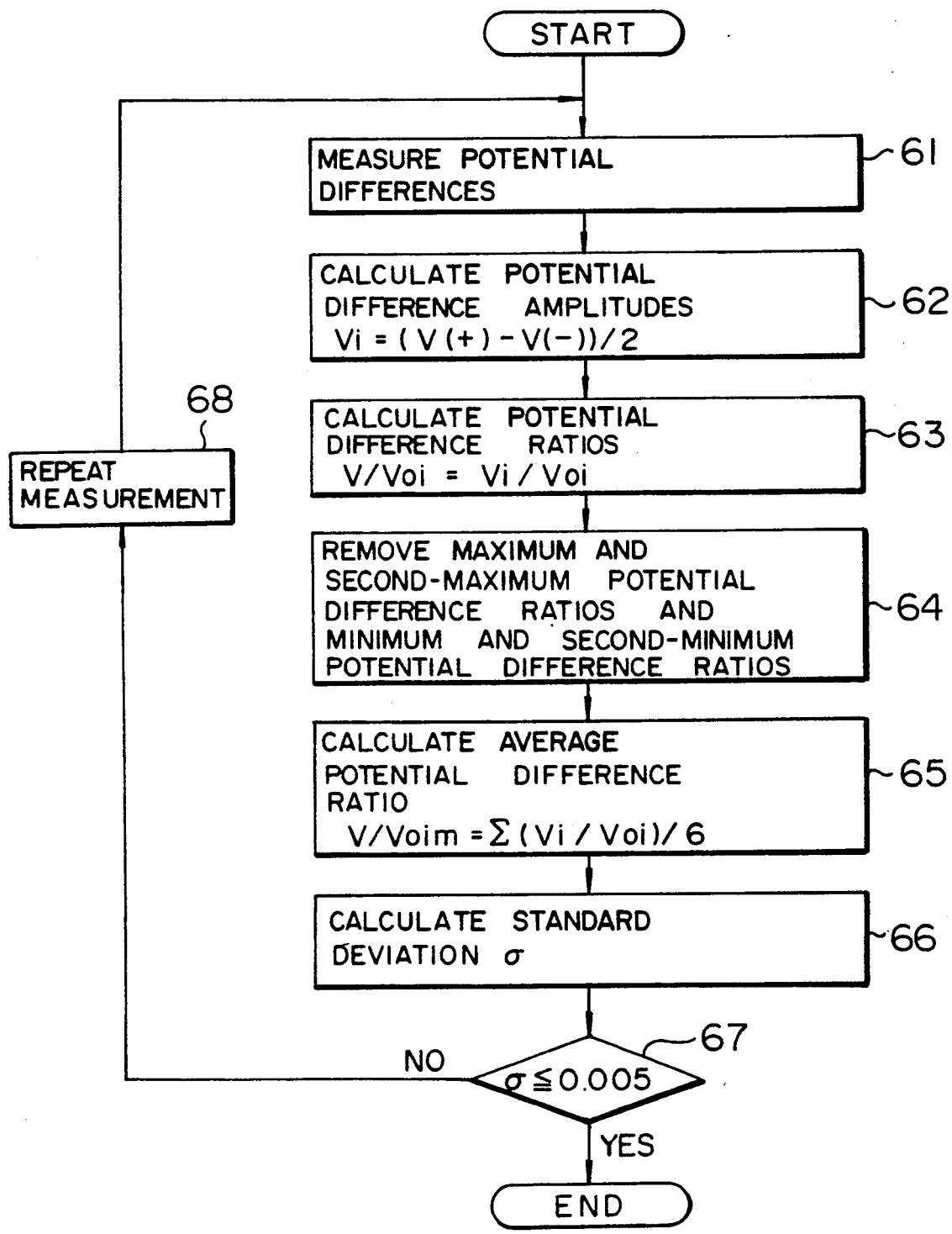
FIG. 16 is a flow chart of the process of judging abnormal measured value of potential difference.

FIG. 16 is a flow chart of a subroutine used for judging the measured values of potential difference. At step 61, the potential differences are measured in accordance with the flow chart of FIG. 15 and, then, at step 62, potential difference amplitudes $V_i=((V(+)-V(-))/2$ and $V_{0i}=((V_0(+)-V_0(-))/2$ are calculated. At step 63, potential difference ratios $(V/V_{0i})=V_i/V_{0i}$ are calculated. At step 64, considering the scattering of potential difference, the maximum and second-maximum potential difference ratios and the minimum and second minimum potential difference ratios are removed. Then at step 65, an average potential difference ratio $(V/V_{0im})=\Sigma(V_i/V_{0i})/6$ is calculated from remaining six potential difference ratios. At step 66, a standard deviation $\sigma$ of the potential difference ratio is calculated and, at step 67, if it is judged to be greater than 0.005, for example, that is, the measurement is abnormal, the operation returns to step 61 through step 68 at which the measurement is repeated again.

Figure 17:
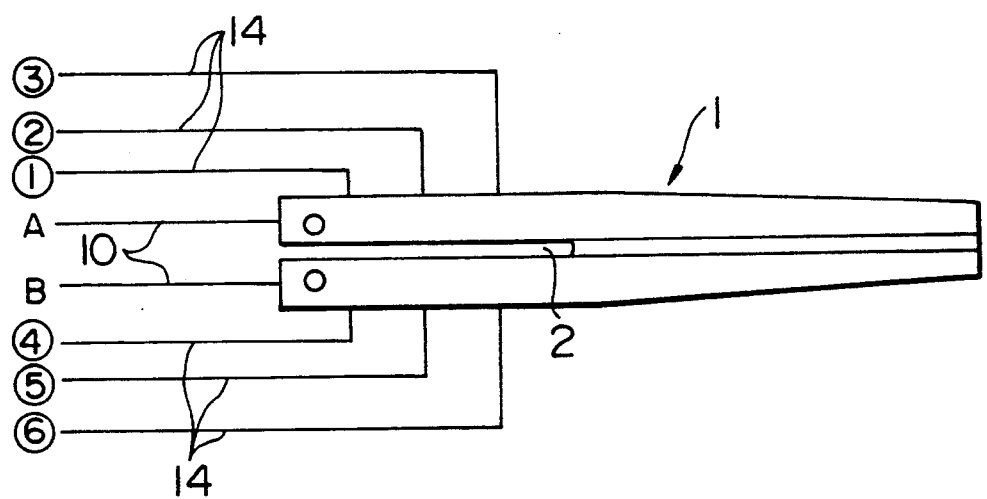
FIG. 17 is a schematic view showing attaching positions of leads to the DCB sensor.

Next, description will be given of a method for detecting the crack length due to the potential difference measurement. FIG. 17 illustrates the wiring of the leads 14 for potential difference measurement use. The direct current supplying leads 10 are attached by spot welding to the DCB sensor 1 near the centers of left side faces thereof and are denoted by symbols A, B in FIG. 17. At least three leads 14 for potential difference measurement use are attached by spot welding to each of opposite outer faces of the DCB sensor 1 with the slit 2 sandwiched therebetween. For discrimination, these leads are denoted by marks and ①, ②, ③, ④, ⑤ and ⑥, respectively. The potential difference is measured between any two of these leads. Expressing the respective potential differences with only the lead number suffixed, fifteen potential differences $V_{12}$, $V_{13}$, $V_{14}$, $V_{15}$, $V_{16}$, $V_{23}$, $V_{24}$, $V_{25}$, $V_{26}$, $V_{34}$, $V_{35}$, $V_{36}$, $V_{45}$, $V_{46}$, and $V_{56}$ are measured. Since the leads 14 are welded equidistantly from each other and positioned symmetrically on opposite sides, it is basically affirmed that $V_{12}=V_{23}=V_{45}=V_{56}$, $V_{13}=V_{46}$, $V_{15}=V_{24}$, $V_{16}=V_{34}$, and $V_{26}=V_{35}$ However, there are differences attributable to the error in attaching of the respective leads. Accordingly, in order to improve the accuracy of the measurement of the crack length, it is the most suitable to obtain an average value of the crack length obtained from many potential differences utilizing master curve representing the relationship between the potential difference and the crack length.

On the other hand, the potential difference is affected not only by the material of the DCB sensor but also temperature. To remove the effects of the material and temperature, it is known to measure the potential differences at two points and obtain the ratio $V/V_0$ of these potential differences, one of which serves as a reference potential difference $V_0$. Using the ratio $V/V_0$ thus obtained prevents the master curve representing the relationship between the potential difference ratio $V/V_0$ and the crack length from being affected by the material and temperature. In the DCB sensor, the reference potential differences are six including $V_0=_{12}\approx V_{23}\approx V_{45}\approx V_{56}$, $V_{13}\approx V_{46}$, and the active potential differences are nine including $V=V_{14}$, $V_{15}=V_{24}$, $V_{16}\approx V_{34}$, $V_{25}$, $V_{26}\approx V_{35}$, $V_{36}$. Therefore, it is understood that there are $6\times 9=54$ combinations of potential difference ratio in all. However, as mentioned before, the reference potential differences are basically two including $V_0=V_{12}=V_{23}=V_{45}=V_{56}$ and $V_0=V_{13}=V_{46}$ and the operating potential differences are six including $V=V_{14}$, $V_{15}=V_{24}$, $V_{16}=V_{34}$, $V_{25}$, $V_{26}=V_{35}$, and $V_{36}$. Therefore, it will do to form $2\times 6=12$ master curves in all representing the relationship between the potential difference ratio and the crack length. In addition, it is proved fundamentally that $V_{13}=V_{46}=2V_{12}=2V_{23}=2V_{45}=2V_{56}$. Therefore, in case that $V_{13}=V_{46}$ is used as the referential potential difference in regard to the same crack length, if the active potential differences are doubled, it is possible to utilize master curves obtained when $V_{12}=V_{23}=V_{45}=V_{56}$ is used as the reference potential difference. Consequently it will essentially do to form six master curves in all representing the relationship between the potential difference ratio $V/V_0$ and the crack length.

Figure 18:
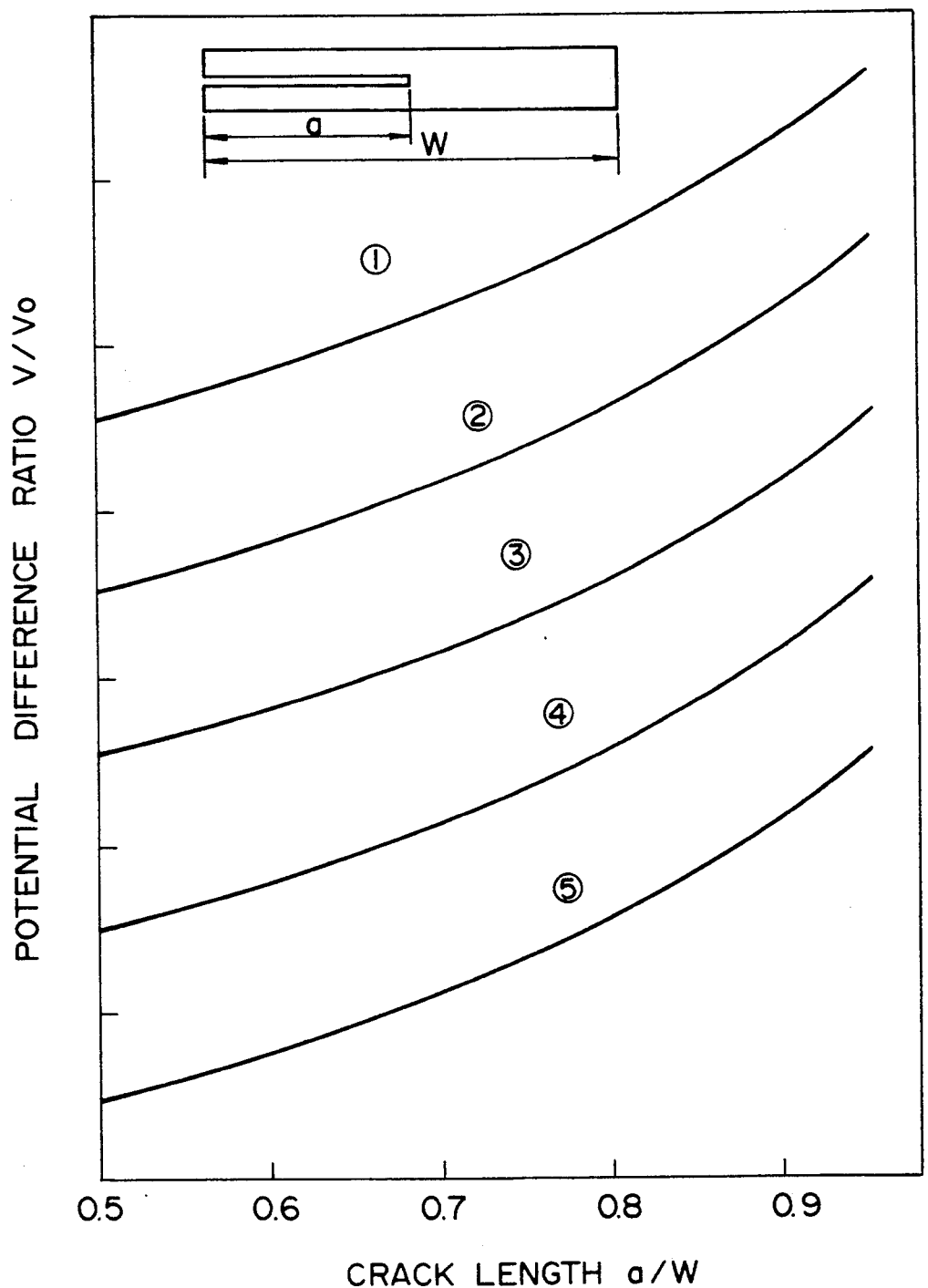
FIG. 18 is a graphical illustration of master curves of the relationship between potential difference ratio and crack length.

FIG. 18 is a graphical illustration depicting characteristics of master curves used for judging the crack length obtained due to electric field analysis using the finite-element method. The ordinate represents the potential difference ratio $V/V_0$ and the abscissa represents the crack length a/W normalized by the length W of the DCB sensor. Curves ①, ②, ③, ④, ⑤ and ⑥ corresponds to $V/V_0=V_{14}/V_{12}$, $V/V_0=V_{15}/V_{12}$, $V/V_0=V_{25}/V_{12}$, $V/V_0=V_{16}/V_{12}$, $V/V_0=V_{26}/V_{12}$, and $V/V_0=V_{36}/V_{12}$, respectively. Each master curve usually approximate with or fifth power equation and the approximate formula obtained is used for converting the potential difference ratio $V/V_0$ into the crack length a/W.

Since the leads 14 for the potential difference measurement are equidistantly welded to each of the opposite outer faces of the DCB sensor 1, it results in $V_{14}=V_{36}+4V_{12}$, $V_{15}=V_{36}+3V_{12}$, $V_{16}=V_{36}+2V_{12}$, $V_{24}=V_{36}+3V_{12}$, $V_{25}=V_{36}+2V_{12}$, $V_{26}=V_{36}+V_{12}$, $V_{34}=V_{36}+2V_{12}$ and $V_{35}=V_{36}+V_{12}$. Accordingly, the master curve for the relationship between the potential difference ratio $V/V_0$ and the non-dimensional crack length a/W is obtained by approximating, in particular, the relationship of $V/V_0=V_{36}/V_{12}$ with a/W by the use of the following fifth power equation.

$$V/V_0 = V_{36}/V_{12} = A_0 + A_0 + A_1(a/W) + A_2(a/W)^2 + A_3(a/W)^3 + A_4(a/W)^4 + A_5(a/W)^5$$

The following results from the above relationship.

The master curve for Curve ④ is given by the following equation:

$$V/V_0 = V_{25}/V_{12} = V_{35}/V_{12} = 1 + A_0 + A_1(a/W) + A_2(a/W)^2 + A_3(a/W)^3 + A_4(a/W)^5.$$

The master curve for Curve ③ is given by the following equation:

$$V/V_0 = V_{16}/V_{12} = V_{25}/V_{12} = V_{34}/V_{12} = 2 + A_0 + A_1(a/W) + A_2(a/W)^2 + A_3(a/W)^3 + A_4(a/W)^4 + A_5(a/W)^5.$$

The master curve for Curve ② is given by the following equation.

$$V/V_0 = V_{15}/V_{12} = V_{24}/V_{12} = 3 + A_0 + A_1(a/W) + A_2(a/w)^2 + A_3(a/W)^3 + A_4(a/W)^4 + A_5(a/W)^5.$$

The master curve for curve ① is given by the following equation.

$$V/V_0 V_{16}/V_{12} = 4 + A_0 + A_1(a/W) + A_2(a/W)^2 + A_3(a/W)^3 + A_4(a/W)^4 + A_5(a/W)^5.$$

Thus there are obtained five master curves. Basically it suffices to find one master curve.

Figure 19:
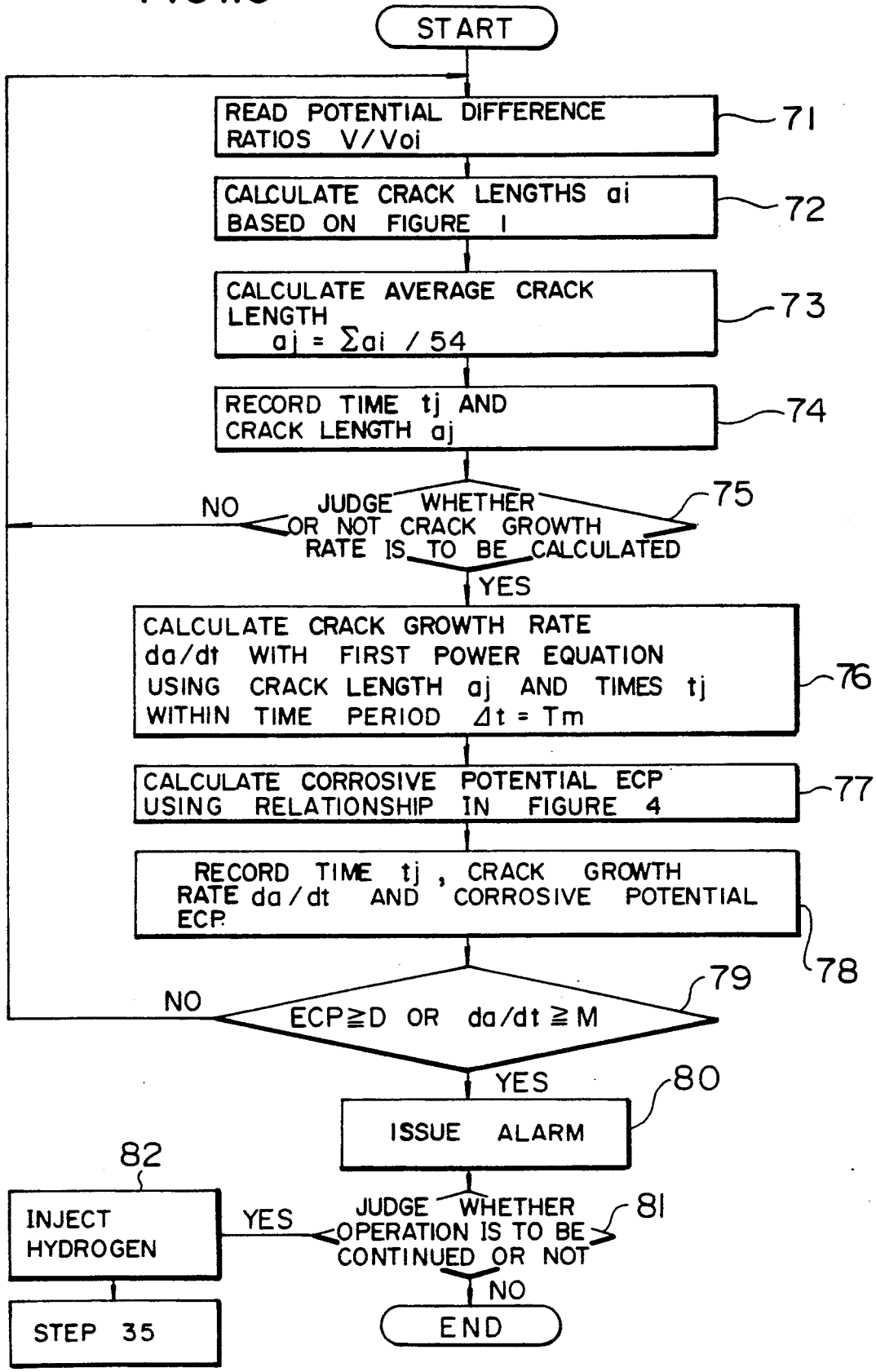
FIG. 19 is a flow chart of the process of crack growth rate judgement and corrosive potential difference measurement.

After a series of crack length measurements have been finished, it becomes necessary to perform the data processing. As shown in FIG. 13, measuring of the crack length in the DCB sensor 1 is controlled completely by the computer 20 so that it is possible to perform the data processing as well. FIG. 19 is a flow chart showing the process of judging the crack length, calculating the crack growth rate and measuring the corrosive environment. At step 71, the potential difference ratios $V/V_0$ are read. At step 72, crack lengths ai are calculated based on the master curves of FIG. 18. At step 73, an average crack length aj is obtained in accordance with the formula $\Sigma ai/54$. Then at step 74, a crack length measuring time tj and the crack length aj are recorded. The crack growth rate should not necessarily be calculated each time the crack length is measured but may be calculated at regular certain time intervals. At step 75, it is judged whether or not the crack growth rate is to be calculated, and if it is judged not to be calculated, the operation returns to step 71. If it is judged that the crack growth rate is to be calculated, the operation proceeds to step 76 at which a crack growth rate da/dt is calculated with a first power equation by a least squares method using the data on the crack lengths aj and times tj obtained and measured within a fixed time period $\Delta t = Tm$. Then, at step 77, a corrosive potential ECP is calculated from the crack growth rate using the relationship shown in FIG. 4. At step 78, the time tj, the crack growth rate da/dt and the corrosive potential ECP are recorded. At step 79, the corrosive environment is judged in accordance with the standard of judgement of $ECP \geq D$ or $da/dt \geq M$. It is noted here that symbols D and M represent critical values in ascertaining whether or not the environment is good. If $ECP < D$, and $da/dt < M$, the operation returns again to step 71, while if $ECP \geq D$ or $da/dt \geq M$, the operation proceeds to step 80 at which an alarm is issued. At step 81, it is judged whether or not the operation is to be continued. If it is judged to continue the operation, the operation proceeds to step 82 at which measures are taken to reduce the concentration of dissolved oxygen by injecting hydrogen into the corrosive environment, for example, and then, the operation returns to step 35 (see FIG. 14) so as to be continued.

Figure 20:
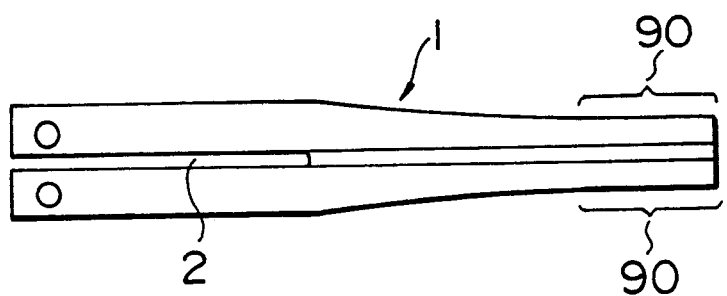
FIG. 20 is a front view of a DCB sensor according to another embodiment of the invention.

In FIG. 20 the shape of the crack growing section is the same as that of the sensor shown in FIG. 10 or 12; and however, the shape of the tapered faces of the external form is different. More specifically, outer faces of the DCB sensor 1 which are parallel to the section in which the crack grows are tapered from a point thereof corresponding to the crack growth starting point with fixed portions 90 thereof which are located on the right of this DCB sensor 1D made to be parallel to the section in which the crack grows, thereby enabling the stress intensity factor to be reduced.

Figure 21:
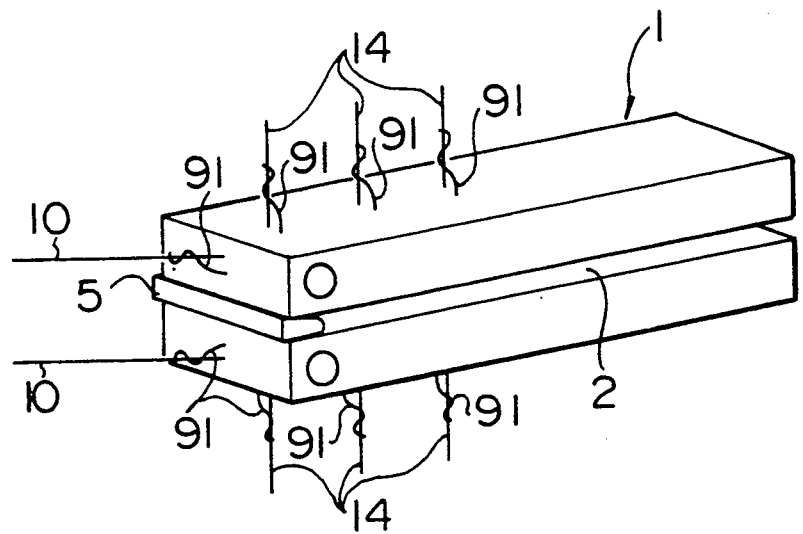
FIG. 21 is a perspective schematic view showing how to attach leads to the DCB sensor.

FIG. 21 provides a possibility, in case of measuring the corrosive environment within high temperature pure water, that the leads 10, 14, attached by spot welding, are broken at the spot welds. If the leads 10, 14 are broken, it becomes impossible to send the electric current to the DCB sensor 1 and measure the potential differences, resulting in that the measurement of the crack length cannot be performed. For this reason, in order to enable the measurement to be performed even if the leads are broken, short leads 91 are wired in addition to the leads 10, 14 connected with the direct current power supply and the microvoltmeter, with the respective leads 91 being spot-welded at one end thereof near the respective leads 10, 14 and wound at the other end thereof around these leads so as to be electrically connected therewith. The leads may be electrically connected with each other by spot welding.

Figure 22:
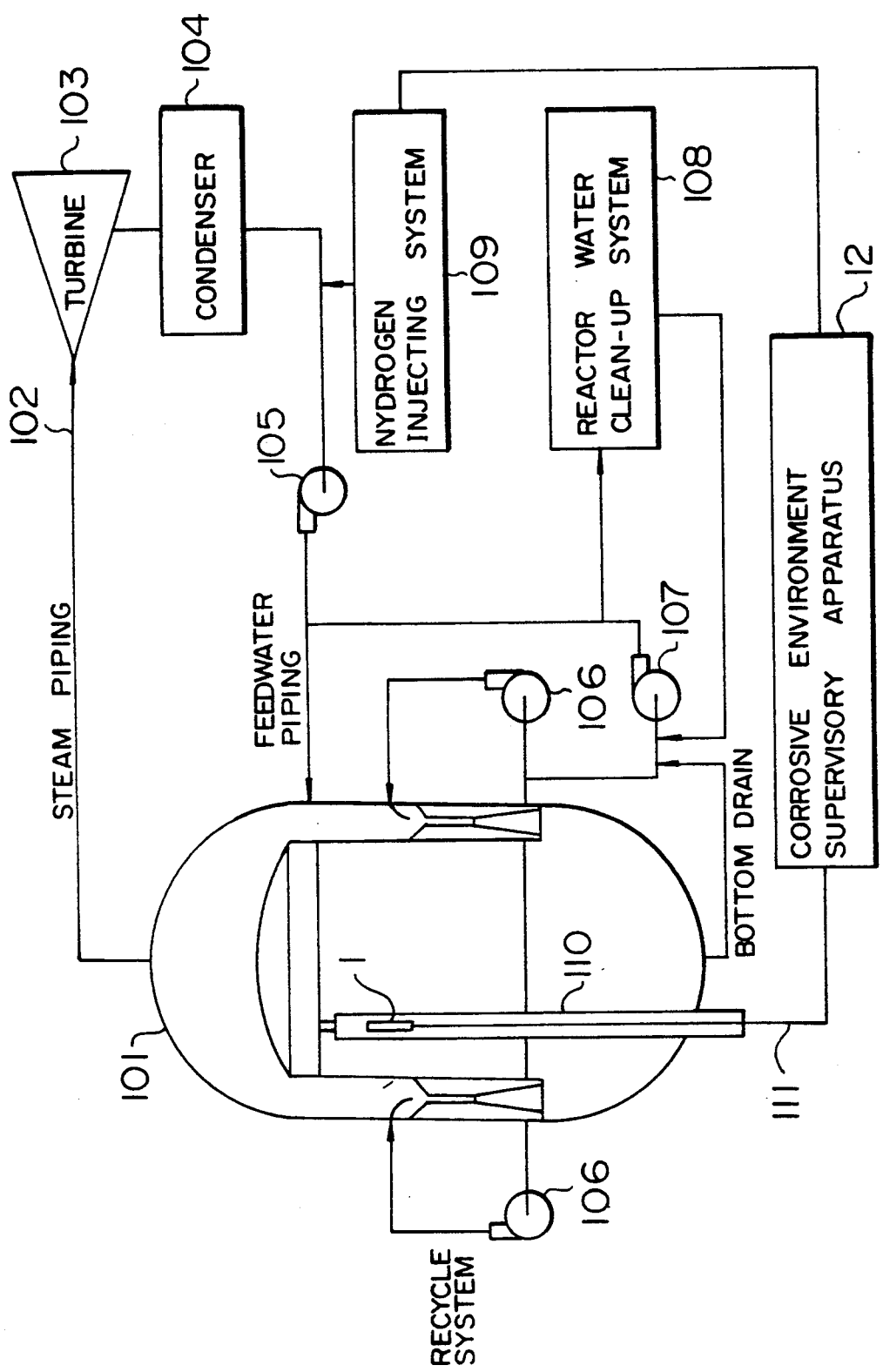
FIG. 22 is a schematic view of a system for measuring crack length and corrosive potential applied to a boiling water type reactor.

FIG. 22 shows an example of boiling water type reactor to which the corrosive environment supervisory apparatus 12 of the present invention is applied for serving to measure the crack length and monitor the water chemistry. The boiling water type reactor system includes a pressure vessel 101 reactor, main steam piping 102, a turbine 103, a condenser 104, a reactor feed water pump 105, a primary loop recirculation pump 106, a reactor water cleanup pump 107, a reactor water cleanup system 108, a hydrogen injecting system 109, a neutron instrument pipe 110, the DCB sensor 1, and the corrosive environment supervisory apparatus 12. In the fuel assembly section of the reactor in which the neutron flux density is high, the DCB sensor 1 is disposed inside the neutron instrument pipe 110 so as to be exposed to the reactor water environment. A cable 111, formed by bundling the current supplying leads 10 and potential difference measuring leads 14, is disposed between the DCB sensor 1 and the corrosive environment supervisory apparatus 12. After measuring the potential differences of the DCB sensor 1, the crack growth rate and the corrosive environment are judged in accordance with the processes shown in FIGS. 14, 15, 16 and 19. If it is judged that the water chemistry is bad, the hydrogen injecting system is operated to inject hydrogen into reactor water through the feed water system, thereby improving the water chemistry of the reactor water.

As seen from the above description, according to the present invention, by providing necessary tapered forms to the section of the crack growing portion of the DCB sensor and to the outer faces of the DCB sensor, the stress intensity factor of the DCB sensor can be made constant. Further, such stress intensity factor constant type DCB sensor is placed in the reactor water of the boiling water type reactor so as to measure the crack length in that sensor using a direct current potential method. Consequently, it is possible to evaluate the corrosive environment with high accuracy over a long time in any of the method for evaluating the corrosive environment directly from the crack growth rate, the method for evaluating the corrosive environment indirectly after estimating the corrosive potential from the crack growth rate, and the method for controlling the corrosive environment by injecting hydrogen based on the result of such evaluation.

What is claimed is:

1. A double-cantilever beam test device for determining a growth rate of a crack with a corrosive environment, the double-cantilever beam test device comprising:
    means for applying a load to the test device by a fixed displacement; and
    a crack growing section for enabling a determination of the growth rate of the crack, said crack growth rate section having a tapering cross-section with a width of the cross-section being reduced as a length of the crack increases.

2. A double-cantilever beam test device according to claim 1, wherein said test device is provided with outer side surfaces extending in parallel to said crack growth section, said outer side surfaces are tapered such that a width of a portion of said side surfaces in a direction crossing a longitudinal direction of said test device is reduced as the length of the crack increases, whereby a stress intensity factor following a growth of the crack is nearly constant.

3. A double-cantilever beam test device according to claim 1, wherein said test device is provided with outer surfaces extending perpendicular to said crack growing section, said outer surfaces are tapered such that a width of a portion of said side surfaces in a direction crossing a longitudinal direction of said test device is reduced as the length of the crack increases, whereby a stress intensity factor following a growth of the crack is nearly constant.

4. A double-cantilever beam test device according to claim 1, wherein said test device is provided with outer surfaces extending in parallel to said crack growing section and further surfaces perpendicular to said outer side surfaces, and said further surfaces are tapered such that a width of portions of said outer side surfaces and said further surfaces in a direction crossing a longitudinal direction of said test device is reduced as a length of the crack increases, whereby a stress intensity factor following a growth of the crack is nearly constant.

5. A double-cantilever beam type test device according to claim 4, wherein a shape of every taper of the crack growing section, the outer side surfaces, and the further surfaces of the test device is a straight line.

6. A double-cantilever beam test device according to claim 4, wherein a starting point of every taper of the outer side surfaces, and the further surfaces are located at a portion of the test device defining an end surface of the crack growing section.

7. A double-cantilever beam test device according to one of claims 1, 2, 3, 4 or 6, wherein a shape of the taper of the crack growing section is at least one curve determined by a second power equation.

8. A double-cantilever beam test device according to claim 7, wherein said shape of said taper of said crack growing section includes two types of curves defined by a second power equation.

9. A double-cantilever beam test device according to one of claims 1, 2, 3 or 4, wherein the width of said crack growing section is gradually reduced from a starting point of the crack growing section and increased near an end point of the crack growing section, as viewed in the longitudinal direction of the test device.

10. A double-cantilever beam test device according to one of claims 2 or 6, wherein said outer side surfaces are tapered from a point corresponding to a starting point of the crack growing section and are parallel to the crack growth section near an end point of the crack growth section.

11. A corrosive environmental crack length measuring apparatus comprising:
    a double-cantilever beam test device according to one of claims 2, 4, 5 or 6 having a slit and at least two holes respectively formed in surface of the test device defining said slit, said test device being placed in a corrosive environment;
    leads inserted into said holes and spot-welded thereto for supplying a direct current to said holes;
    a current polarity switching device;
    a stabilized direct current power supply connected with said leads through said current polarity switching device;
    potential difference measuring leads inserted in holes formed in said outer side surfaces at a plurality of points in a crack growing direction and spot-welded thereto;
    a multiplexer;
    a micro-voltmeter connected with said potential difference measuring leads through said multiplexer; and
    arithmetic and processing means for judging a length of the crack based on ratios between potential differences measured by switching the polarity of direct current using said current polarity switching device.

12. A corrosive environmental crack length measuring apparatus according to claim 11, further comprising additional holes formed in said test device near spot-welded positions of said respective direct current supplying leads and potential difference measuring leads, and relatively short leads each being spot welded to one of said additional holes at one end thereof and connected electrically with a corresponding one of said direct current supplying leads and potential difference measuring leads by spot-welding or twisting.

13. A corrosive environmental crack length measuring apparatus according to claim 11, wherein six potential difference measuring leads are provided and potential differences between three leads attached to each outer side surface of said test device provide reference potential differences so that the length of the crack is judged based on ratios of potential differences between three leads attached to one of the outer side surfaces and three leads attached to the other outer side surface and said reference potential differences.

14. A corrosive environmental crack length measuring apparatus according to claim 13, wherein the length of the crack is judged based on an average crack length calculated by substituting the ratios obtained from the six reference potential differences and nine potential differences into a predetermined between the length of the crack and potential difference ratio.

* * * * *